(12) United States Patent
DiFiglia et al.

(10) Patent No.: US 6,602,673 B2
(45) Date of Patent: *Aug. 5, 2003

(54) HUNTINGTIN-RELATED THERAPEUTICS AND BIOASSAY

(75) Inventors: Marian DiFiglia, Newton, MA (US); Neil Aronin, Newton, MA (US); James Velier, Strafford, PA (US)

(73) Assignees: University of Massachusetts, Boston, MA (US); The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 75 days.

(21) Appl. No.: 08/970,734

(22) Filed: Nov. 14, 1997

(65) Prior Publication Data

US 2001/0007753 A1 Jul. 12, 2001

Related U.S. Application Data

(60) Provisional application No. 60/030,940, filed on Nov. 15, 1996.

(51) Int. Cl.[7] .............................................. G01N 33/53
(52) U.S. Cl. ....................................... 435/7.21; 435/7.2
(58) Field of Search ................................. 435/7.21, 7.2

(56) References Cited

FOREIGN PATENT DOCUMENTS

EP        0 614 977 A        9/1994

OTHER PUBLICATIONS

Rudinger. In "Peptide Hormones" (ed. J. A. Parsons) University Park Press, Baltimore, pp. 1–7, 1976.*
DiFiglia, et al., "A Protein Related to Human Huntingtin is Associate with Transport Vesicles in Rat Brain Neurons," Abstract; *Molecular Biology of the Cell*, vol. 5:474A, 1194 (1995).
Duyao, et al., "Inactivation of the Mouse Huntington's Disease Gene Homolog Hdh," *Science*, vol. 269:407–410, Jul. 21, 1995.
Augood S.J. et al., "Reduction in enkephalin and substance . . . ," Neuroscience, 72(4):1023–1036, 1996.
Aronin et al., "Clues To Huntingtin's Normal and Abnormal Function", *J. NIH Research*, 7(9):55–56, 1995.
Aronin et al., "CAG Expansion Affects the Expression of Mutant Huntingtin in the Huntington's Disease Brain", *Neuron*, 15:1193–1201, 1995.
Bhide et al., "Expression of Normal and Mutant Huntingtin in the Developing Brain", *J. Neuroscience*, 16(17):5523–5535, 1996.
Carter et al., "Multiple GTP–binding Proteins Participate in Clathrin–coated Vesicle–mediated Endocytosis", *J. Cell. Biol.*, 120(1):34–35, 1993.
DiFiglia et al., "Huntingtin Is a Cytoplasmic Protein Associated with Vesicles in Human and Rat Brain Neutrons", *Neuron*, 14:1075–1081, 1995.
Gutekunst et al., "Identification and localization of huntingtin in brain and human lymphoblastoid cell lines with anti–fusion protein antibodies", *Proc. Nat'l. Acad. Sci. USA* 92(19):8710–8714, 1995.
Sapp et al., "Huntingtin Localization in Brains of Normal and Huntington's Disease Patients", *Annuals of Neurology*, 42(4):604–612, 1997.
Scherzinger et al., "Huntingtin–Encoded Polyglutamine Expansions Form Amyloid–like Protein Aggregates In Vitro and In Vivo", *Cell*, 90(3):549–558, 1997.
Sharp et al., Widespread Expression of Huntington's Disease Gene (IT15) Protein Product, *Neuron*, 14(5):1065–1074, 1995.
Smythe et al., "Cytosol – and Clathrin–dependent Stimulation of Endocytosis In Vitro by Purified Adaptors", *J. Cell. Biol.*, 119(5):1163–1171 (1992).
Velier et al., "Wild–Type and Mutant Huntingtin Localize to the Golgi Complex and to Vesicles in the Peripheral Cytoplasm in Fibroblasts of control and HD Patients", *Soc. of Neuroscience*, vol. 22, Abstract 92.3, 1996.

* cited by examiner

*Primary Examiner*—Gary L. Kunz
*Assistant Examiner*—Robert C. Hayes
(74) *Attorney, Agent, or Firm*—Fish & Richardson P.C.

(57) ABSTRACT

A method of identifying a compound useful in the treatment of a disease characterized by the presence of mutant huntingtin by: (a) providing a cell which expresses mutant huntingtin; (b) contacting the cell with a test compound; and (c) determining whether the level of clathrin-mediated endocytosis is increased in the presence of the test compound, compared to the level in the absence of the test compound. An increase in clathrin-mediated endocytosis is an indication that the test compound is useful in treating the disease.

7 Claims, 9 Drawing Sheets

HUNTINGTIN    CLATHRIN

HUNTINGTIN-RELATED THERAPEUTICS AND BIOASSAY

CROSS REFERENCE TO RELATED APPLICATIONS

This application claims priority from U.S. provisional Application Ser. No. U.S. Ser. No. 60/030,940, filed Nov. 15, 1996.

STATEMENT AS TO FEDERALLY SPONSORED RESEARCH

This invention was made with Government support under Contract Numbers NS16367 and NS31579 awarded by the National Institutes of Health. The Government may have certain rights in this invention.

BACKGROUND OF THE INVENTION

Huntington's Disease (HD) is an autosomal dominant neurodegenerative disorder that causes progressive motor and cognitive impairments in its victims, ultimately leading to death (Wexler et al., Ann. Rev. Neurosci. 14:503–529, 1991; Folstein, In Huntington's Disease: A Disorder of Families. Johns Hopkins University Press, pages 1–64, 1989). Although widespread abnormalities in the HD brain have been reported, the striatum is the most severely affected structure, exhibiting marked atrophy and loss of neurons, particularly of medium-sized spiny cells (Graveland et al., Science 227:770–773, 1985; Vonsattel et al., J. Neuropath. Exp. Neurol. 44:559–577, 1985).

The link between the genetic change in HD and processes leading to cell death remain elusive. The gene associated with HD, IT15 (for interesting transcript 15), was isolated (The Huntington's Disease Research Collaborative Group, Cell 72:971–983, 1993) and shown to predict a 348 kDa protein, huntingtin. The HD-causing mutations in IT15 involve an expansion of a trinucleotide (CAG) repeat encoding glutamines near the 5' end of the coding sequence. In general, individuals with 37 or more repeats will get Huntington's disease. IT15 bears no homology to other known genes, and its function in disease is unknown.

The normal biological role of wild-type huntingtin is also unknown. This role is presumed to be important because deletion of both huntingtin genes in the mouse leads to death on about the seventh embryonic day (E7), before the brain is formed (Duyao et al., Science 269:407–409, 1995).

Huntingtin is found in soluble and membrane-associated compartments in cells. In synaptosomal membrane fractions of the HD brain, mutant huntingtin is apparently present at levels comparable to the wild-type protein (Aronin et al., Neuron 15:1193–1201, 1995; Aronin et al., J. NIH Res. 7:55–56, 1995). This observation implies that both proteins are anterogradely transported and associated with the same intracellular membranes. A major obstacle to identifying the potential sites of protein interactions of mutant huntingtin is distinguishing its subcellular location from that of the wild-type protein. This cannot be done in brain, where only heterozygote tissue is currently available.

SUMMARY OF THE INVENTION

As described herein, the subcellular distribution of wild-type and mutant huntingtin overlaps that of clathrin. Thus, wild-type huntingtin may play a critical role in the process of clathrin-mediated endocytosis. Furthermore, when a mutant form of huntingtin is expressed, as occurs in Huntington's Disease, the characteristic impairment and eventual death of neurons that ensues may be caused by a defective endocytotic process. The invention involves identifying compounds that may remedy defects in the endocytotic process associated with the presence of mutant huntingtin.

The invention features a method of identifying a compound useful in the treatment of a disease characterized by the presence of mutant huntingtin by: (a) providing a cell which expresses mutant huntingtin; (b) contacting the cell with a test compound; and (c) determining whether the level of clathrin-mediated endocytosis is increased in the presence of the test compound compared to the level in the absence of the test compound. An increase in clathrin-mediated endocytosis is an indication that the test compound is useful in treating the disease.

The test compound can be a compound that activates either GTP-binding proteins or protein kinase C (e.g., a phorbol ester). Alternatively, the test compound can be a compound that alters the pH (e.g., raising the pH by at least 0.5 pH units, and preferably by 1.0 pH units) or the concentration of calcium in the extracellular environment.

Cells to be used in the invention can be obtained from a patient who has been diagnosed as having Huntington's Disease. The presence of 37 or more of the CAG repeats in the huntingtin gene are diagnostic of Huntington's Disease. Because the disease is dominant, a person need only have one copy of the gene to get Huntington's Disease. Furthermore, the disease is virtually 100% penetrant. Therefore, a person diagnosed as having Huntington's disease is a person who has an expanded CAG repeat region in at least one of their huntingtin genes although that person may have no or few symptoms of the disease at the time of diagnosis. Alternatively, the cells may be any cells that express mutant huntingtin including cells that have been genetically engineered. Preferably, the cells are fibroblasts. More preferably, the cells are neurons.

The level of clathrin-mediated endocytosis can be determined by monitoring the amount of a substance taken up from the extracellular medium in a given amount of time. This can be measured, for example, by monitoring the uptake of biotinylated transferrin (b-transferrin) and its receptor, as described herein, and may reflect a change in the rate of an endocytotic step.

The invention also features a method of determining whether a compound is useful for treatment of a patient who has been diagnosed as having Huntington's Disease. In practicing this method, one would obtain appropriate cells from the patient, contact those cells with the compound, and determine whether the level of clathrin-mediated endocytosis is increased in the presence of the compound, compared to the level in a control sample in the absence of the compound. An increase in clathrin-mediated endocytosis is an indication that the compound is useful in treating the patient.

Although methods and materials similar or equivalent to those described herein can be used in the practice or testing of the present invention, the preferred methods and materials are described below. These methods, materials, and examples are illustrative only and not intended to be limiting.

All publications, patent applications, patents, and other references mentioned herein are incorporated by reference in their entirety.

Other features and advantages of the invention will be apparent from the following detailed description, and from the claims.

BRIEF DESCRIPTION OF THE DRAWINGS

FIGS. 1A–B is a pair of photographs of Western blots in which huntingtin expression is assessed with the antibody Ab 2527. Protein extracts (20 μg/lane) of human fibroblasts and human brain and of mouse brain were prepared. (C)= control tissue; (HD)=Huntington's Disease tissue. The HD patients from which the tissue was obtained were heterozygote juveniles with large (60 or greater) CAG repeat expansions. As shown in the left-hand panel (A), wild-type huntingtin is detected in all lanes at its predicted molecular mass of about 350 kDa. Huntingtin in mouse brain runs slightly faster than human huntingtin, which is consistent with the smaller mass predicted for the mouse protein. Mutant huntingtin appears as the upper band in the HD tissues and migrates more slowly than the wild-type due to CAG repeat expansion in the HD allele. Preadsorption with peptide antigen, shown in the right-hand panel (B), blocks detection of huntingtin by Ab 2527. The position of a molecular weight marker (at 208 kDa) is shown on the left and right sides of each panel.

In FIG. 2A, punctate vesicular labeling is present around the nucleus (Nuc) and throughout the cytoplasm. The fibroblasts shown in FIGS. 2B and 2C were double-labeled for the 58 kDa Golgi-associated protein and huntingtin. Arrows point out the overlapping distribution of the two proteins within the Golgi complex.

FIGS. 3A and 3B illustrate the distribution of these proteins in the absence of bfa (−bfa). The staining around the nucleus is concentrated in a membrane-like labyrinth characteristic of the Golgi-complex. FIGS. 3C and 3D illustrate the distribution of these proteins in the presence of bfa (+bfa). Localization of both proteins is more widely dispersed from the nucleus and the Golgi-membrane architecture is disrupted.

FIG. 5A illustrates huntingtin staining adjacent to the nucleus (n) and discrete clusters of punctate labeling (arrows). FIG. 5B is an electron micrograph of the perinuclear region, which demonstrates that the labeled clusters seen at the light microscopic level consist of groups of heavily labeled clathrin-coated vesicles (arrows). Scale bar in 5B=0.1 μm.

In FIG. 6A, total protein extracts from fibroblasts of a normal individual, three HD homozygous patients, and two heterozygous juvenile patients illustrate the presence of wild-type and/or mutant huntingtin. Each case is identified at the top of the column by the CAG repeat number for each allele. Repeat numbers of 39 or more CAGs are in the HD range. FIG. 6B shows huntingtin expression in fraction 5 from heterozygous juvenile HD patient shown in FIG. 6C. Both wild-type and mutant proteins are comparably expressed. In FIG. 6C, Nycodenz™ (Accurate Chemical & Scientific Corp., Westbury, N.Y.) gradient fractions from a normal individual (wild-type) and HD homozygous and heterozygous patient fibroblasts are shown. Wild-type and mutant huntingtin are maximally expressed at about 350 kDa in low density fractions (number 3–number 7). Wild-type and mutant protein co-segregate with clathrin heavy chain, which migrates at about 190 kDa, and with a portion of transferrin receptor, which migrates at about 190 kDa for the dimer. Most of the transferrin receptor is segregated in fractions at the high density end of the gradient. The position of molecular weight markers are shown on the right-hand side of panels 6A–6C.

In FIG. 8A, the cell body and emerging processes show a punctate vesicular labeling. In FIG. 8B, the plasma membrane of a labeled cell body shows marked punctate labeling (arrows) consistent with a distribution in coated pits and vesicles. In FIG. 8C, labeled neurites show abundant vesicular-like labeling within the cytoplasm and along the plasma membrane (arrowheads). In FIG. 8D, immunoperoxidase staining is highly concentrated on coated vesicles (arrows) in the right-hand panel; the left-hand panel shows unlabeled coated vesicles (arrows) along another region of the plasma membrane of the same cell.

FIG. 9A is an electron micrograph showing the cisternae and vesicles of the Golgi complex in a pyramidal neuron. Huntingtin-labeled large coated vesicle (large arrow) and other unlabeled coated vesicles (small arrows) are present. In FIG. 9B, a large coated pit budding into a dendrite exhibits reaction product along the plasma membrane and interspersed within the triskelia of the coat. For comparison, see the unlabeled coated pit in FIG. 9C, which buds from the plasma membrane of a nearby dendrite. In FIG. 9D, a huntingtin-positive coated vesicle (arrow) in a dendrite appears to bud from an unlabeled membranous organelle. In FIG. 9E, a large huntingtin labeled coated vesicle in a dendrite shows a sparse but distinct peroxidase reaction product over the membrane and within the clathrin coat. Arrowheads mark the boundary of the dendrite and the plasma membrane, which was evident in adjacent sections. Open arrow identifies an unlabeled coated vesicle in a neighboring axon terminal. All scale bars=0.1 μm.

DETAILED DESCRIPTION

It has been found that there is an overlap between the localization of huntingtin and clatherin thus indicating a role for huntingtin in endocytosis. The invention tests compounds for their ability to affect endocytosis in the presence of a mutant huntingtin gene. Compounds that affect endocytosis (e.g., increase it) are candidates for therapeutic agents for treatment of Huntington's disease.

In order to study the biological role of huntingtin, the subcellular locations of wild-type and mutant huntingtin were determined by several procedures. For example, anti-huntingtin antisera identified the membranous organelles with which wild-type and mutant huntingtin interact. Huntingtin also localized to clathrin-coated vesicles in the cell bodies (soma) and processes of immortalized mouse striatal neurons and cortical neurons in situ, and was detected by Western blot analysis in purified fractions of clathrin-coated vesicles from rat brain. Immunoblots of subcellular membrane fractions confirmed that both wild-type and mutant huntingtin were concentrated with clathrin in the same membrane fractions. In addition, confocal microscopy was performed on normal fibroblasts and fibroblasts obtained from HD patients with one (heterozygote) or two (homozygote) mutant alleles. This analysis revealed that the distribution of wild-type and mutant huntingtin "overlapped" with the distribution of clathrin at the trans Golgi network (TGN) and in coated pits and vesicles at the plasma membrane. Thus, huntingtin may participate in clathrin-mediated processes at multiple sites within the endocytic pathway. For example, in neurons affected by HD, mutant huntingtin may impair clathrin-dependent processes, including protein transport from the TGN, and hinder the interaction of ligand-bound receptors at the plasma membrane.

Cells to be used in the invention can be acquired directly from patients having at least one mutant huntingtin gene or from cell repositories such as the Coriell Cell Repositories (Camden, N.J.). Cells can also be engineered to contain a mutant huntingtin gene using methods known to those in the art. Vectors to be used in making such recombinant cells can be constructed by recombinant DNA technology methods known in the art (e.g., Ausubel et al.,"Current Protocols in Molecular Biology, Vol. I," Green Publishing Associates, Inc., and John Wiley & Sons, Inc., NY, 1989). Vectors can be plasmid, viral, or others known in the art, used for replication and expression in mammalian cells. Expression of the sequence encoding a huntingtin gene can be by any promoter known in the art to act in mammalian, preferably human cells. Such promoters can be inducible or constitutive. One such promoter that can be used in the invention is the Tet-on or Tet-off promoter (Clontech, Palo Alto, Calif.) described below. Constructs may also be contained on an artificial chromosome (Huxley, Trends. Genet. 13:345–347, 1997).

The huntingtin sequence used in a construct can include either a complete or partial coding sequence. If a partial coding sequence is used, it encodes the N-terminus of huntingtin and includes the expanded repeat (CAG) region of a mutant huntingtin gene. Such sequences are known in the art and can be found in, for example, GenBank. Additional details for preparing transfected cells are in Example V.

Cells used in the invention are cultured according their cells types. The cultured cells described in the Examples below were prepared as follows.

Cell Culture

For immunohistochemical studies, normal and HD patient fibroblasts were obtained from Coriell Cell Repositories (Camden, N.J.). The cells were plated onto 12 mm round coverslips (Bellco Glass Inc., Vineland, N.J.) coated with poly-L-lysine, then grown in Falcon petri dishes (Fisher Scientific, Pittsburgh, Pa.) at 37° C. with 5% $CO_2$. The cells were cultured with modified Eagle's medium (Gibco BRL, Grand Island, N.Y.) supplemented with L-glutamine, penicillin-streptomycin, and 20% fetal bovine serum. In HD cells, the presence of the CAG repeat was confirmed using the PCR assay of Goldberg et al. (Human Mol. Genet. 2:635–636, 1993) as described in Aronin et al. (Neuron 15:1192–1201, 1995; J. NIH Res. 7:55–56, 1995). When cells were grown for the purpose of isolating of genomic DNA, they were cultured in 10 cm plastic petri dishes.

Immortalized striatal cells (X57, X58) were obtained by somatic cell fusion of mouse embryonic striatal neurons and N18TG2 neuroblastoma cells. These cells were plated onto glass coverslips and grown under the conditions described by Wainwright et al. (J. Neurosci. 15:676–688, 1995). Neurite outgrowth was induced by treating the cells for three days with 10 $\mu$M forskolin.

Immunohistochemistry

For the studies described herein, fibroblasts from passage number 10–15 were plated onto coverslips and grown in culture for 24–48 hours. Cells were rinsed briefly with phosphate buffered saline (PBS) and fixed for 10 minutes with 4% paraformaldehyde in PBS at room temperature. After fixation, cells were rinsed multiple times and stored at 4° C. in PBS. Huntingtin was immunolocalized in human fibroblasts using an affinity purified anti-peptide antibody, Ab 2527, at 2–4 $\mu$g/ml. In selected experiments, cells were also labeled with a monoclonal antiserum that recognizes clathrin heavy chain (2 $\mu$g/ml, Biodesign Int., Kennebunk, Me.), the Golgi-associated 58 kDa protein (ascites serum diluted 1:100, Sigma Chemical Co., St. Louis, Mo.), or human transferrin receptor (5 $\mu$g/ml, Zymed Laboratories Inc., San Francisco, Calif.). Cells were made permeable by a 30 minute incubation in 0.1% Triton® X-100 in PBS, rinsed several times, and blocked with 5% normal goat serum for 60 minutes prior to incubation in primary antibodies. All incubations, whether performed with a single type of antibody or two types of antibodies, were carried out overnight at 4° C. and were followed by multiple rinses in PBS. Secondary antibodies were used at a 1:400 dilution. A pooled mixture of either Texas Red goat anti-mouse IgG (Molecular Probes Inc., Eugene, Oreg.) and Bodipy FL anti-rabbit IgG (Molecular Probes Inc, Eugene, Oreg.) or Texas Red goat anti-mouse IgM (Vector Laboratories, Burlingame, Calif.) and Bodipy FL anti-rabbit IgG were used. For immunoperoxidase labeling, cells were rinsed several times after the primary incubation and an avidin/biotin blocking procedure was performed prior to the incubation in secondary antibody. A Vectastain ABC™ kit (Vector Laboratories, Burlingame, Calif.) was employed to localize the primary antibody, and diaminobenzidine was used as a substrate for visualization of the peroxidase reaction product. Sections were examined using conventional immunofluorescence microscopy and a Biorad 1024 laser confocal microscope. Image processing was performed with Adobe Photoshop™.

Generation of anti-huntingtin antisera

Two of the anti-huntingtin antisera used, Ab 1 and Ab 585, were characterized previously (DiFiglia et al., Neuron 14:1075–1081, 1995). Ab 1 was generated against amino acids 1–17 of huntingtin and Ab 585 was generated against amino acids 585–745 of huntingtin. To generate Ab 2527, the peptide-antigen containing amino acids 2527–2547 of human huntingtin was coupled at the N-terminus to keyhole limpet hemocyanin, and the antibody production schedule in rabbits and the peptide affinity purification of the collected serum were performed as previously described for anti-peptide huntingtin antisera 1 and 2911 (DiFiglia et al., Neuron 14:1075–1081, 1995).

Electron Microscopy

Fibroblasts and striatal hybrid cells were grown on coverslips made from Aclar (Ted Pella, Inc., Redding, Calif.) (instead of glass) and fixed in 4% paraformaldehyde in 0.1 M PBS for 10 minutes. The immunoperoxidase method described previously for cultured neurons (Zhou and DiFiglia, Exp. Neurol. 122:171–188, 1993) was applied, using Ab 1 as the primary antiserum to detect immunoreactive huntingtin (DiFiglia et al., Neuron 14:1075–1081, 1995). Cells grown on the Aclar coverslips were post-fixed in 1% osmium tetroxide, stained with 1% uranyl acetate, dehydrated, and infiltrated with Epon resin. The embedded monolayer of cells on Aclar coverslips was then placed cell-side down on glass slides coated with a releasing agent (Ted Pella, Inc.). Areas were selected from the embedded monolayer and mounted onto blank Epon blocks. Thin sections were cut and mounted on mesh grids for examination in the electron microscope using methods known to those in the art (see also, for example, Glauert, ed. Practical Methods in Electron Microscopy, North Holland Publishing Company, New York, N.Y., 1975; Robards and Wilson, eds., Procedures in Electron Microscopy, John Wiley & Sons, New York, N.Y., 1993).

Immunoperoxidase labeling for huntingtin and electron microscopic analysis of mouse cortex using Ab 585 was accomplished as previously described for the rat and mouse brain (DiFiglia et al., Neuron 14:1075–1081, 1995; Bhide et al., J. Neurosci. 16:5523–5535, 1996).

EXAMPLE I

Distribution of wild-type and mutant huntingtin in human fibroblasts

Figure 1:
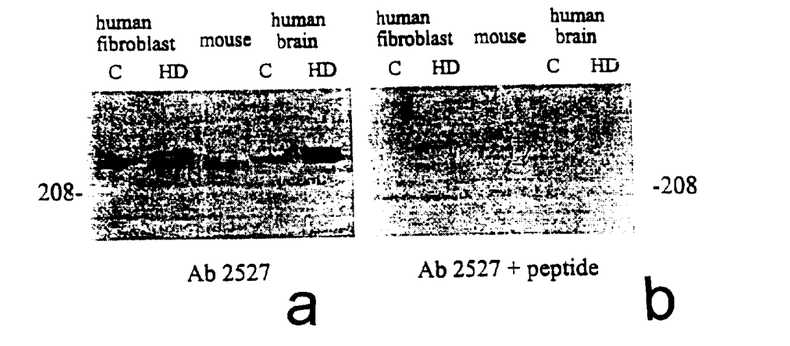
Figure 2:
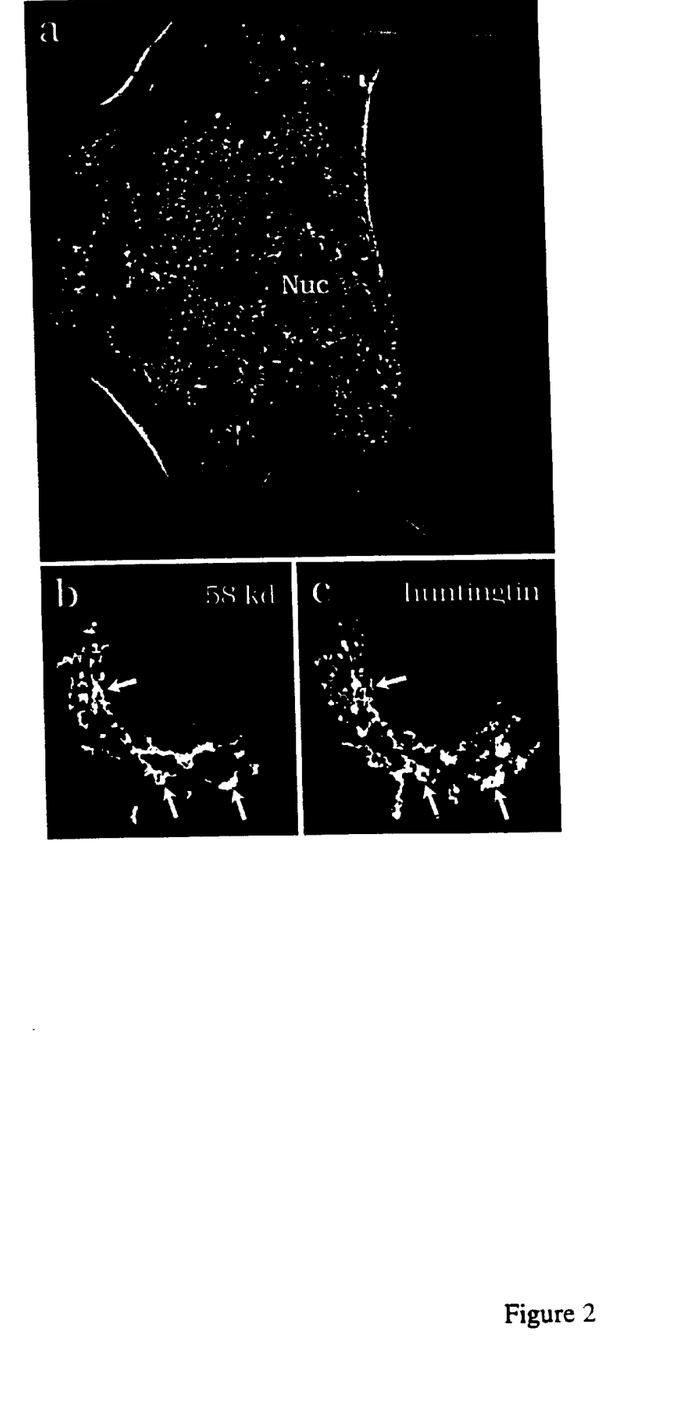
FIGS. 2A–2C are photographs of control fibroblasts stained with Ab 2527, as observed with confocal microscopy.

Expression of wild-type and mutant huntingtin in fibroblasts and brain was revealed by Western blot analysis using the antibody Ab 2527 (generated against amino acids 2527–2547 of human huntingtin). Immunofluorescence confocal microscopy with Ab 2527 showed dense labeling of vesicular membranes in the perinuclear and peripheral cytoplasm of normal fibroblasts and those from HD patients with one (heterozygote) or two (homozygote) mutant alleles. Pre-incubation of primary antisera with peptide antigen blocked the detection of huntingtin by Western blot (FIG. 1) and immunohistochemistry. To determine if the perinuclear staining for huntingtin was in the Golgi apparatus, and not in endoplasmic reticulum (ER) or endosomal membranes positioned around the nucleus, cells were double-labeled to detect huntingtin and the 58 kDa protein, which marks Golgi membranes (FIGS. 2B and 2C, shown for wild-type only). Results showed an overlap in distribution of the two proteins, indicating that huntingtin's perinuclear distribution was within the Golgi complex.

Brefeldfin A (BFA) treatment of human fibroblasts

To further establish the association of huntingtin with Golgi membranes, cells were treated with the fungal metabolite Brefeldin A (BFA).

Cells were briefly rinsed with Hank's balanced salt solution (HBSS) and then incubated in complete medium containing BFA (5 µg/ml; Gibco/BRL). The cells were incubated at either 18° C. or 37° C. for 10 minutes, then rinsed briefly with 50 mM phosphate buffered saline (PBS; pH 7.4) and fixed immediately for 10 minutes with 4% paraformaldehyde in PBS at room temperature.

Figure 3:
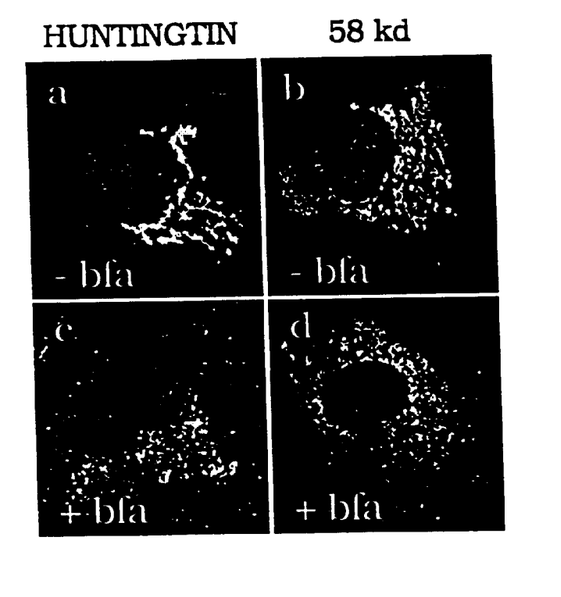
FIGS. 3A–3D are a series of photographs illustrating the effect of Brefeldin A (bfa) on huntingtin and the 58 kDa protein in normal fibroblasts.

Treatment with BFA inhibits vesicle transport between Golgi compartments and at the exit of the Golgi pathway in the trans Golgi network (TGN; Klausner et al., J. Cell Biol. 116:1071–1080, 1992; Robinson et al., Cell 69:129–138, 1992) by interfering with the assembly of coat proteins (β-COP, clathrin) needed for budding. Huntingtin was fragmented and dispersed by mild BFA treatment (5 µg for 10 min at 18° C.; FIGS. 3A and 3B) and obliterated by more severe BFA treatment. BFA treatment had similar effects on the localization of the 58 kDa protein (FIGS. 3C and 3D). The distribution of tubulin in BFA-treated cells was unchanged compared to untreated cells.

Figure 4:
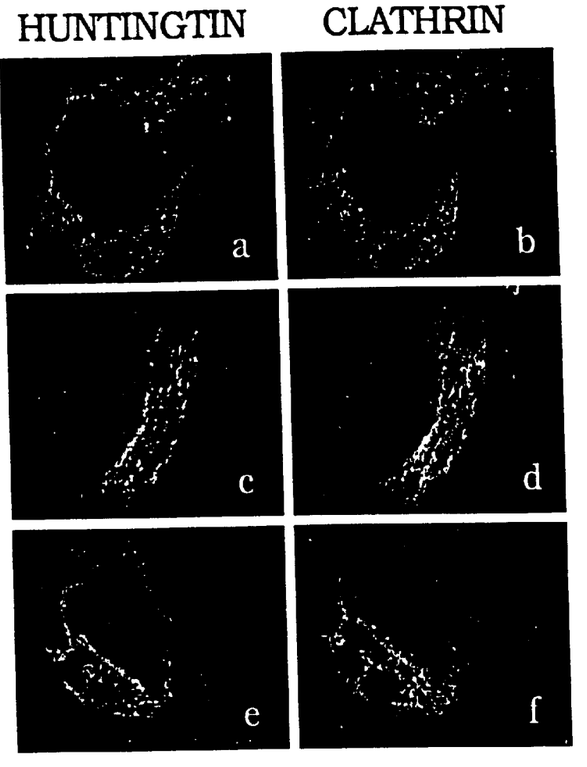
FIGS. 4A–4F are a series of photographs illustrating immunofluorescence analysis of huntingtin and the heavy-chain subunit of clathrin in the trans-Golgi network (TGN) of control (healthy) and Huntington's Disease patient fibroblasts. Double-immunofluorescence shows that huntingtin overlaps with clathrin in the perinuclear cytoplasm of normal (4A and 4B), homozygous (4C and 4D), and heterozygous (4E and 4F) patient cells. Huntingtin was detected with Ab 2527.

Huntingtin's localization in the Golgi region was compared to that of clathrin, a coat protein that assembles on membranes in the TGN (Pley et al., Mol. Biol. 28:431–464, 1993). In human fibroblasts and other cultured cells fixed with paraformaldehyde, clathrin-labeled membranes distribute in a "reticulum" around the nucleus as well as in punctate vesicular structures within the cytoplasm (Kartenbeck et al., Exper. Cell Res. 133:191–211, 1981). Immunofluorescence labeling followed by confocal microscopy of control and HD patient fibroblasts demonstrated that huntingtin and clathrin overlapped in the perinuclear region (FIG. 4).

Figure 5:
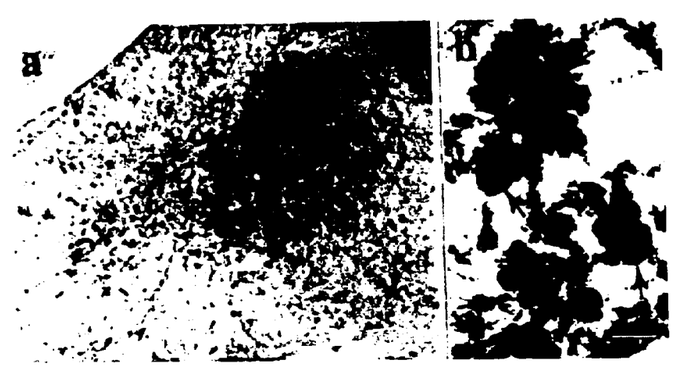
FIGS. 5A and 5B are a pair of photographs illustrating huntingtin labeling in a normal fibroblast with the immunoperoxidase method and Ab 2527 as the primary antisera.

Immunoperoxidase labeling with Ab 2527 produced the same punctate perinuclear staining seen with immunofluorescence. (FIG. 5A). Electron microscopic examination of the immunoperoxidase product showed that huntingtin was highly concentrated on clusters of large coated vesicles (FIG. 5B).

To determine whether any of the immunoreactive huntingtin in vesicles of the peripheral cytoplasm co-distributed with clathrin, cells were double-stained to detect both antigens. Regions of overlap between immunoreactive huntingtin vesicles and clathrin-stained vesicles (or coated pits) were found adjacent to and within the plasma membrane of long cytoplasmic extensions of both normal and HD patient cells. There were vesicular organelles labeled by huntingtin and clathrin antisera which did not overlap. However, the correlation of huntingtin and clathrin in vesicles within and adjacent to the plasma membrane provides strong evidence that huntingtin is positioned to function in the early stages of receptor-mediated endocytosis. To further explore this possibility, the potential co-distribution of huntingtin-enriched vesicles and transferrin receptor, a receptor protein that cycles between the plasma membrane and early endosomal compartments (Hopkins et al., J. Cell Biol. 97:508–521, 1983; Trowbridge and Hopkins, J. Cell Biol. 97:508–521) was investigated. As with clathrin and huntingtin, vesicles containing transferrin receptor and huntingtin were detected along the plasma membrane and within the underlying cytoplasm of the distal extensions of the fibroblasts. Vesicular organelles containing only huntingtin or transferrin receptor were also present. No overlap between huntingtin and transferrin receptor was found in the perinuclear region of the cell, where both proteins were concentrated. The co-localization of huntingtin with transferrin receptor at the plasmalemma provides support for huntingtin's role in receptor-mediated endocytosis.

EXAMPLE II

Western blot analysis of subcellular membrane fractions of normal and HD patient fibroblasts The cells described above were prepared for this series of experiments as follows. Once confluent monolayers formed in culture, the cells were harvested. Five 10 cm dishes containing cultured cells were washed twice with Dulbecco's Phosphate Buffered Saline (DPBS) then scraped with a rubber policeman in 500 µl of homogenization buffer (10 mM triethanolamine, 10 mM acetic acid, 250 mM sucrose, 1 mM ethylenediaminetetraacetic acid (EDTA), 1 mM dithiothreitol (DTT) and 10 µg/ml each of aprotinin, leupeptin, pepstatin, and chymostatin (pH 7.4). The final volume was approximately 3 ml. All of these steps were carried out on ice.

To homogenize the cells, they were passed through a 25-gauge needle (on a 3 ml syringe) 10 times and then homogenized in a Dounce Homogenizer. Unbroken cells and debris were removed by centrifugation at 1500×g for 5 minutes. The postnuclear supernatant was concentrated by centrifugation at 75,000×g for 30 minutes. The supernatant ("soluble fraction") was collected, and the pellet was resuspended in 1 ml of 5% Nycodenz™ in 10 mM HEPES NaOH buffer (pH 7.4) using a micro pestle. Nycodenz™ gradients were prepared according to the method of Hammond and Helenius (J. Cell Biol. 126:41–52, 1994). Gradients were made a day in advance as step gradients containing 500 µl 60% sucrose and 2.5 ml each of 24%, 19.33%, 14.66%, and 10% Nycodenz™. The solutions were prepared from a 50% Nycodenz™ stock in 10 mM HEPES NaOH buffer (pH 7.4). To diffuse the gradient, the tubes were stored at 4° C. overnight. The postnuclear supernatant, resuspended in 5% Nycodenz™, was loaded on the top of the gradient and centrifuged for 4 hours at 37,000 rpm in Beckman L8-M centrifuge fitted with an SW 41 TI rotor. Seventeen fractions were collected from each gradient and the gradient profile was determined using the protein concentration of each fraction. Twenty µl of each fraction, including the soluble fraction, were loaded in gel loading buffer (50 mM Tris pH 6.8, 2% SDS, 0.1% bromphenol blue, 10% glycerol, 100 mM DTT) on a 10% polyacrylamide gel with 0.5% bisacrylamide (Aronin et al., Neuron 15:1193–1201, 1995; Aronin et al., J. NIH Res. 7:55–56, 1995). For analysis of the transferrin receptor, DTT was omitted from the gel loading buffer, allowing the 190 kDa dimer to remain intact. The proteins were transferred onto nitrocellulose for 75 minutes and immunoblotted with anti-huntingtin (Ab 1) or antitransferrin receptor (Zymed Laboratories) followed by secondary antisera and enhanced chemiluminescence (Amersham, Arlington Heights, Ill.) for protein detection. Blots used to detect huntingtin were reprobed for clathrin heavy chain (Biodesign, Int.).

Figure 6:
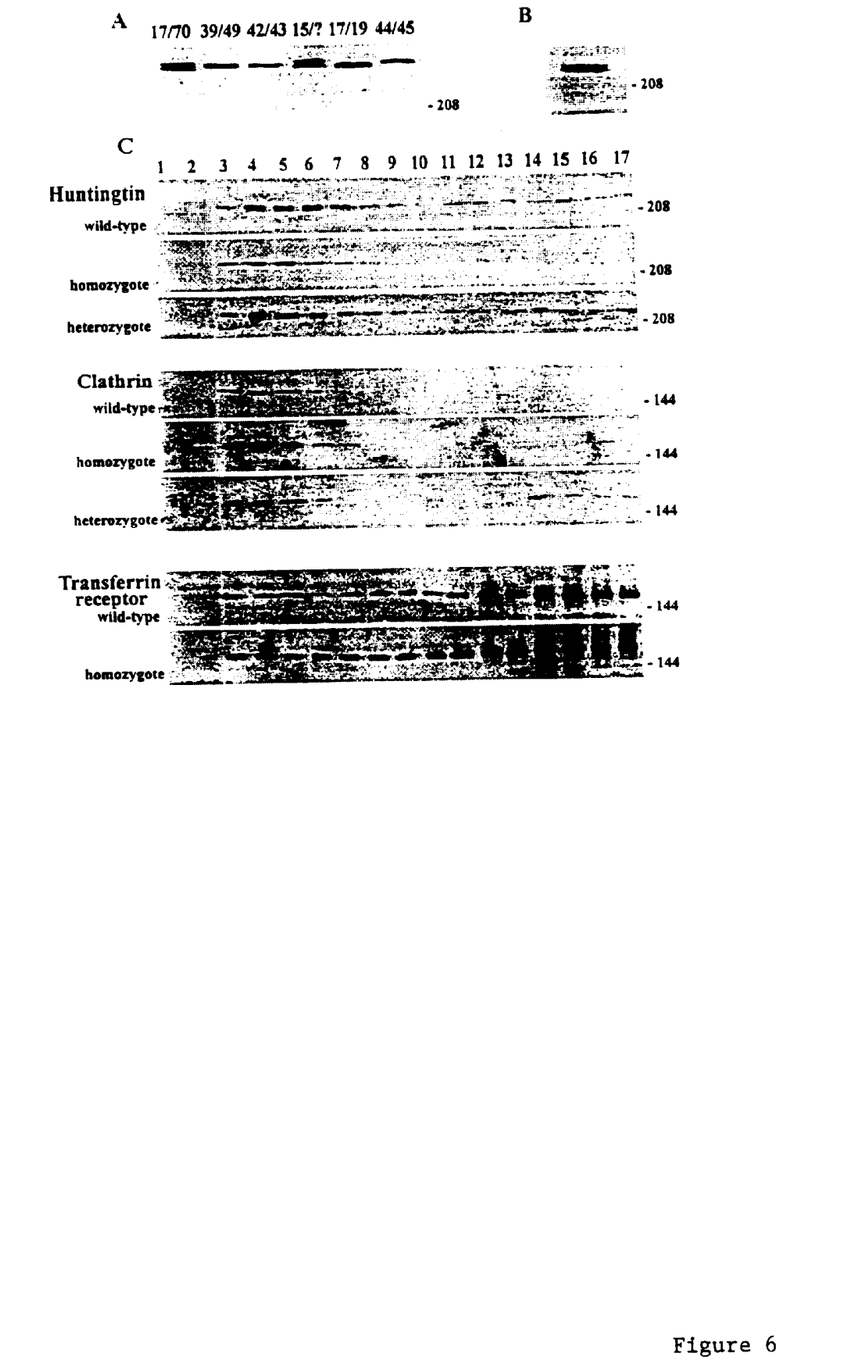
FIGS. 6A–6C are a series of photographs of Western blots in which huntingtin in total protein and subcellular membrane fractions of human fibroblasts is analyzed with Ab 1.

Analysis of total protein extracts from control fibroblasts and HD homozygote and heterozygote patient fibroblasts showed that mutant huntingtin was clearly distinguishable from wild-type by its slower mobility due to the presence of the expanded polyglutamine region (FIG. 6A). To examine subcellular membranes, immunoblots were performed on postnuclear supernatants of three normal and three HD patient cell lines which had been separated by equilibrium density ultracentrifugation in a continuous Nycodenz™ gradient (FIG. 6B). Results in all cases were the same. Wild-type huntingtin in normal fibroblasts and mutant huntingtin in homozygote and heterozygote HD patient cells were maximally detected at the light end of the density gradient (fractions 3–7) and occurred at much lower levels in some of the higher density fractions. There was no evidence that mutant huntingtin segregated differently from wild-type huntingtin in heterozygotes with large CAG repeats of the HD allele (FIG. 6C, fraction 5) or in homozygotes, in which only mutant protein was expressed. Maximal huntingtin expression corresponded with the peak expression of clathrin at the lowest third of the gradient (fraction numbers 3–7). Transferrin receptor was present in low density fractions with huntingtin and clathrin, although its expression was maximal in membrane fractions in the upper third of the gradient. The cell fractionation results suggest that in human fibroblasts, CAG expansion does not change the membrane compartments with which huntingtin is associated. In addition, these observations support the findings with immunofluorescence demonstrating the co-localization of wild-type or mutant huntingtin with clathrin and transferrin receptor.

EXAMPLE III

Immunoblot analysis of huntingtin in clathrin-coated vesicles isolated from rat brain Immunoblot analysis and immunogold labeling have shown an association of huntingtin with vesicular membranes (DiFiglia et al., Neuron 14:1075–1081, 1995; Gutekunst et al., Proc. Natl. Acad. Sci USA 97:8710–8714, 1995). To determine whether huntingtin is found with clatherin-containing vesicles in the brain, coated vesicles were isolated from whole rat brain according to the protocol described by Pearse (Methods in Cell Biology, Academic Press, San Diego, Calif. 31:229–243, 1989). Rats were killed by decapitation and their brains rapidly removed. A volume of Buffer A (0.1 M (2-[N-morpholino] ethanesulfonic acid)-NaOH (pH 6.5), 0.2 mM ethyleneglycol-bis-(β-amino-ethylether)N,N'-tetraacetic acid, 0.5 mM $MgCl_2$, 0.02% $NaN_3$, and 0.1 mM phenylmethylsulfonyl fluoride) equal to that of the brain was added, and the mixture was homogenized on ice with a Polytron™ (Brinkman Instruments, Inc., Westbury, N.Y.). This homogenate (H) was centrifuged for 30 minutes at 20,000×g. The supernatant (S1) was removed and centrifuged for 1 hour at 100,000×g to produce supernatant S2 and pellet P2. P2 was resuspended in Buffer A and an equal volume of 12.5% Ficoll (Pharmacia Biotech, Inc., Piscataway, N.J.) and 12.5% sucrose was added. This mixture was centrifuged for 40 minutes at 43,000×g. This produced the Ficoll/sucrose supernatant and the Ficoll pellet. The Ficoll/sucrose supernatant was diluted with 4 volumes of Buffer A and the mixture was centrifuged for 1 hour at 100,000×g, yielding supernatant S3 and pellet P3. P3, enriched in clathrin-coated vesicles, was resuspended in Buffer A.

Electron microscopic analysis confirmed that P2 was a heterogeneous mixture of membranous organelles and that P3 was >95% clathrin-coated vesicles.

Figure 7:
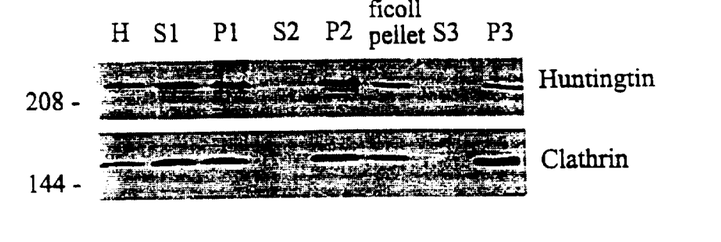
FIG. 7 is a pair of photographs of Western blots in which huntingtin in clathrin-coated vesicles isolated from rat brain are analyzed. Huntingtin and clathrin are found in soluble (S1) and membrane-enriched (P1, P2, and P3) fractions. Huntingtin is maximally expressed in P2, which contains a mixture of coated and uncoated membranous organelles, and is retained in the clathrin-enriched P3 fraction, which has more than 95% coated vesicles as verified by electron microscopic analysis. Each lane was loaded with 20 μg of protein. The positions of molecular weight markers are shown on the left-hand side.

As with clathrin, huntingtin was detected in different subcellular fractions, denoting its presence in the cytosol and in association with vesicle membranes. Huntingtin was most abundant in the fraction containing a mixture of vesicle types ("P2", FIG. 7) and was retained in the clathrin-enriched coated-vesicle fraction ("P3"). These results support the observations made using immunofluorescence and suggest that a portion of the membrane-bound huntingtin in the brain is associated with clathrin-coated vesicles.

EXAMPLE IV

Huntingtin Localization in Mouse Striatal and Cortical Neurons

Figure 8:
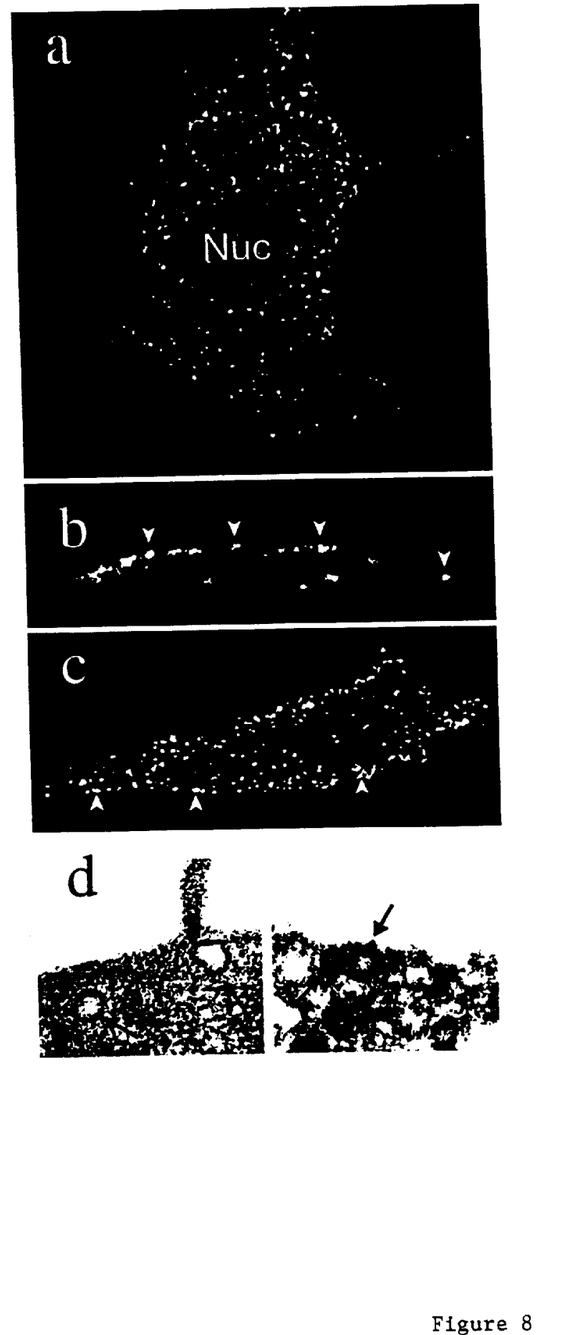
FIGS. 8A–8D are photographs obtained following immunofluorescence confocal microscopy and electron microscopy of huntingtin in immortalized striatal neurons (X58 cell line). Huntingtin was detected with Ab 1.

Cell types are known to vary in the morphology and distribution of membranes belonging to the Golgi complex and the endosomal system (Parton et al., J. Neurosci. Res. 36:1–9, 1993). Thus, to determine how the pattern of huntingtin staining in fibroblasts compared to neurons, immortalized mouse striatal neurons (Wainwright et al., J. Neurosci. 15:676–688, 1995) were examined with anti-huntingtin antisera Ab 1 using methods described above. These cells exhibited little perinuclear concentration of huntingtin but had abundant vesicular labeling throughout the cell bodies and neurites (FIGS. 8A, 8B, and 8C). Significantly, these cells contained numerous labeled vesicles along the plasma membrane of the soma and neurites, suggesting localization of huntingtin in coated pits and early endosomes. Electron microscopy confirmed that immunoreactivity was associated with large coated vesicles in the perinuclear Golgi region and at the plasma membrane (FIG. 8D).

Figure 9:
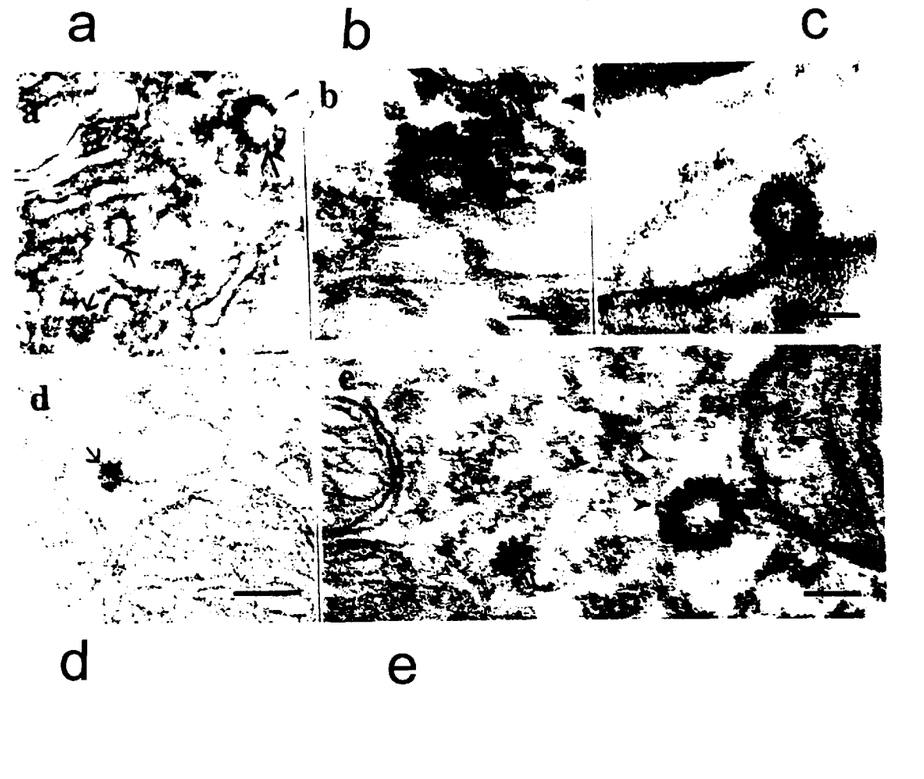
FIGS. 9A–9E are a series of electron micrographs of immunoreactive huntingtin in somatodendritic regions of mouse cortical neurons detected with Ab 585.

The somatodendritic domain of cortical pyramidal neurons is highly enriched in huntingtin immunoreactivity (DiFiglia et al., Neuron 14:1075–1081, 1995; Gutekunst et al., Proc. Natl. Acad. Sci USA 97:8710–8714, 1995; Sharp et al., Neuron 14:1065–1074, 1995). In these cells, immunoreactive huntingtin localized to large and small coated vesicles budding from the TGN (FIG. 9B) and to large (100 nm) coated pits (FIG. 9B) and coated vesicles (FIG. 9E) along the somatodendritic plasma membrane. Small huntingtin-positive coated vesicles appeared to bud from unlabeled cisternae (FIG. 9D). Internalized vesicles within multivesicular bodies (late endosomes) were devoid of staining. These findings demonstrate that in the somatodendritic domain of neurons, huntingtin associates with clathrin-coated membranes.

The Function of Huntingtin in TGN Transport and Endocytosis

The studies described herein demonstrate that, in fibroblasts, wild-type and mutant huntingtin associates with clathrin-coated vesicles in the trans Golgi network (TGN) and with clathrin-coated pits and vesicles at the plasma membrane. Similarly, wild-type huntingtin associates with clathrin-coated membranes in immortalized striatal cells in culture and in cortical neurons in situ.

Clathrin-dependent vesicle budding is important in a variety of cellular functions, including the sorting from the TGN of secretary vesicles and lysosomal enzymes, vesicle trafficking from early endosomes, and receptor-mediated endocytosis at the plasma membrane (Pearse et al., Ann. Rev. Cell Biol. 6:151–171, 1990; Pley et al., Mol. Biol. 28:431–464, 1993; Parton, J. Neurosci. Res. 36:1–9, 1993). Without committing to any particular theory, the findings described herein indicate that wild-type huntingtin has an essential function in endocytosis that is shared by all cells, and that mutant huntingtin acquires properties that interfere with cell processes involved in huntingtin's normal function, especially in neurons.

Huntingtin's interaction with clathrin-coated vesicles strongly supports a biological role for the protein in vesicle transport in neurons (DiFiglia et al., Neuron 14:1075–1081, 1995; Aronin et al., Neuron 15:1193–1201, 1995; Aronin et al., J. NIH Res. 7:55–56, 1995; DiFiglia, 1995). An involvement in endocytic trafficking in somatodendritic regions could explain the prevalence of immunoreactive huntingtin in neuronal cell bodies and dendrites in the brain (DiFiglia et al., Neuron 14:1075–1081, 1995; Gutekunst et al., Proc. Natl. Acad. Sci USA 97:8710–8714, 1995; Sharp et al., Neuron 14:1065–1074, 1995; Bhide et al., J. Neurosci. 16:5523–5535, 1996). The presence of huntingtin-positive coated vesicles in differentiated striatal-hybrid cells, cortical neurons, and fibroblasts, which share characteristics of protein composition with coated vesicles in the somatodendritic domain of the neuron (Parton et al., J. Cell Biol. 119:123–137, 1992; Parton et al., J. Neurosci. Res. 36:1–9, 1993; Dotti, 1993), is compatible with this idea.

Clathrin-dependent, receptor-mediated endocytosis is a dominant function in the somatodendritic portion of a neuron (Parton et al., J. Neurosci. Res. 36:1–9, 1993; Dotti, 1993). Coated membranes bud from the entire plasmalemma and internalize integral membrane proteins including receptors and their ligands (von Zastrow et al., J. Biol. Chem. 267:3530–3538, 1992; Parton et al., J. Cell Biol. 119:123–137, 1992), growth factors (Ferguson et al., J. Neurosci. 10:2176–2189, 1990), and neuropeptides (Mantyh et al., Science 268:1629–1632, 1995; Mantyh et al., Proc. Natl. Acad. Sci. USA 92:2622–2626, 1995; Faure et al., J. Neurosci. 15:4140–4147, 1995). Internalized protein complexes are rapidly directed for further sorting to nearby early endosomes, which form extensive networks and give rise to vesicles that bud through a clathrin-dependent process (Parton et al., J. Cell Biol. 119:123–137, 1992; Stoorvagel et al., J. Cell Biol. 132:21–33, 1996). The rapid internalization of ligand/receptor complexes into dendrites has been shown for transferrin and its receptor in cultured hippocampal neurons (Cameron et al., J. Cell Biol. 115:151–164, 1991; Parton et al., J. Cell Biol. 119:123–137, 1992; Mundigl et al., J. Cell Biol. 122:1207–1221, 1993) and for substance P and its receptor (NK1) in striatal neurons in vivo (Mantyh et al., Proc. Natl. Acad. Sci. USA 92:2622–2626, 1995). Thus, even a subtle defect in clathrin-mediated receptor regulation resulting from the HD mutation could have profound consequences on the function of striatal neurons.

Huntingtin's presence in axon terminals and its co-distribution with synaptic vesicle membrane proteins in synaptosomal fractions (DiFiglia et al., Neuron 14:1075–1081, 1995; Sharp et al., 1995, supra) could indicate involvement with coated vesicles. In axons, clathrin-coated vesicles have a nearly identical membrane protein composition to synaptic vesicles (Maycox et al., J. Cell Biol. 118:1379–1388, 1992), and may form from both internalized endosomal membranes and the plasma membrane (DeCamilli et al., Neuron 16:481–486, 1996; Takei et al., J. Cell Biol. 133:1237–1250, 1996). Coated vesicles in axons are thought to function primarily in the recycling of synaptic vesicles (Maycox et al., 1992), but may also participate in receptor-mediated endocytosis in those neuronal systems that are dependent upon the axonal uptake and retrograde transport of target-derived growth factors, presynaptic receptors, and other signaling molecules.

Huntingtin could influence clathrin-mediated endocytosis at one or more stages, for example at the stages of coat protein assembly, membrane budding, separation of the coated vesicle from the membrane, and vesicle uncoating. A variety of soluble proteins cycle between the cytosol and the membrane in dynamic interactions regulating these early stages of endocytosis. Soluble proteins include clathrin isoforms, adaptor proteins (AP1, AP2, AP180) and GTP-binding proteins (Rab proteins, dynamin, ARFS; Schmid and Smythe, J. Cell Biol. 114:869–880, 1991; Carter et al., J. Cell Biol. 120:37–45, 1993; Cavenagh et al., J. Biol. Chem. 271:21767–21774, 1996). Neuron-specific forms of clathrin light chains, adaptor proteins, and dynamin have also been identified (Jackson et al., Nature, 326:154–159, 1987; Pley and Parham, Crit. Rev. Biochem. Mol. Biol. 28:431–464, 1993; DeCamilli and Takei, Neuron 16:481–486, 1996). Huntingtin's involvement with coated membranes could occur through interactions with one or several of the above proteins. Like many of the other proteins involved in clathrin-mediated endocytosis, huntingtin may have a discrete attachment to endocytic vesicles during one or more stages including an overlap with clathrin. Additionally, clathrin-coated vesicles co-immunoprecipitate with tubulin (Kelly et al., J. Cell Biol. 97:1191–1199, 1983), and therefore may be highly dependent on this cytoskeletal protein for transport and coat assembly. Huntingtin's localization to microtubules, which has been observed by immunogold labeling (Gutekunst et al., Proc. Natl. Acad. Sci. USA 97:8710–8714, 1995), could be related to the transport of coated vesicles.

Implications for Huntington's Disease

The demonstration that mutant huntingtin is distributed to clathrin-coated membranes suggests that HD pathology may arise from a disruption in coat formation or budding in selected neurons in the brain. We have found no evidence for differences between the subcellular distribution of huntingtin in fibroblasts from normal and HD patients. Furthermore, fibroblasts from these two sources appear to grow, divide, and accumulate transferrin comparably.

Subtle defects in the early stages of clathrin-mediated endocytosis may be difficult to detect because these events are very rapid and cells may partially or completely compensate for huntingtin-related deficiencies by using alternative endocytic pathways (Damke et al., J. Cell Biol. 131:69–80, 1995). Neurons may be more dependent upon specific endocytic circuits and may lack the ability to compensate for subtle impairments in the endocytic process. For example, in neurons, G-protein coupled receptors are highly regulated by clathrin-mediated endocytosis. Striatal neurons, which are most affected in HD, are enriched in a variety of neurotransmitter/neuropeptide receptors that are coupled to G-proteins. The severe loss in enkephalin and substance P expression and transport (Sapp et al., Neurosci. 64:397–404, 1995; Richfield et al., Ann. Neurol. 37:335–343, 1995), reduced D1 dopamine receptor binding (Filloux et al., Expl. Neurol. 110:219–227, 1990), and alterations in distal dendrite morphology (Graveland et al., Science 227:770–773, 1985), which are all observed in HD striatal neurons early in the disease, could evolve from a dysfunction in the endocytic pathway.

A marked accumulation of huntingtin-positive tubular membranes and multivesicular bodies has been seen in HD-affected neurons (Sapp et al., Annal. Neurol. 43:604–612, 1997). This alteration may signal a change in the membrane targeting of the protein within the endosomal/lysosomal pathway. Studies of dynamin may be particularly instructive because the distribution of huntingtin, as shown herein, is striking similar to the subcellular distribution to dynamin, which is the best understood of the GTP-binding proteins that are involved in regulating clathrin-mediated endocytosis (Carter et al., J. Cell Biol. 120:37–45, 1993; Henley et al., J. Cell Biol. 133:761–775, 1996; Noda et al., Neurosci. 55:113–127, 1993; Takei et al., J. Cell Biol. 133:1237–1250, 1996; Takei et al., Nature 374:186–190, 1995). In the shibire fly, a mutation in the dynamin gene causes motor dysfunction which is due to a defect in endocytosis. The importance of dynamin in a mammalian system has also been demonstrated: expression of mutant rat dynamin in mammalian cells inhibits the formation and budding of coated vesicles (Damke et al., J. Cell Biol. 127:915–934, 1994; Herskovits et al., J. Cell Biol. 122:565–578, 1993).

EXAMPLE V

Assays for Determining the Level of Clathrin-mediated Endocytosis

The results described above demonstrate an association between both wild-type and mutant huntingtin with clathrin-coated vesicles. HD pathogenesis may involve a defect in the formation or trafficking of coated vesicles leading to difficulties in transport from the TGN, receptor-mediated endocytosis and/or synaptic vesicle recycling. Interactions with brain-specific isoforms of clathrin light chains, adaptor proteins, or GTP-binding proteins could provide the means by which mutant huntingtin functions abnormally to cause selective neuronal degeneration in the HD brain.

Compounds that affect the formation or trafficking of coated vesicles may therefore be useful for treatment of Huntington's Disease. The assays used in the invention for identifying such compounds are based on the observation that the sequestration of transferrin can be used to assay clathrin-mediated endocytosis. Biotinylated transferrin (b-transferrin) is used as a ligand for receptor-mediated endocytosis. In the assays, cells are analyzed both for b-transferrin that is internalized but is in unbudded vesicles, and b-transferrin that is in budded vesicles. Endocytic events are scored by either the inability of a membrane impermeant reducing agent (β-mercaptoethane sulfonate, sodium salt; Sigma Chemical Co.; MesNa), to cleave accessible biotin residues, or the inability of avidin to mask accessible biotin residues. The b-transferrin is captured on antibody-coated microtiter wells and remaining and/or unmasked biotin residues are quantitated using streptavidin conjugated to a detectable marker (such as horseradish peroxidase). The inaccessibility of b-transferrin to MesNa measures only internalization of b-transferrin into sealed coated vesicles while inaccessibility of b-transferrin to exogenously added avidin measures both internalization into sealed coated vesicles and its sequestration in deeply invaginated coated pits. The quantitative difference in signals obtained in the two assays provides a selective measurement of the sequestration of b-transferrin into deeply invaginated coated pits. Test compounds that are candidates for affecting an endocytotic process, especially with respect to those cells with a mutant huntingtin, are tested by adding them to the assays. The principle of these assays can be applied to other proteins that are internalized in a similar way to transferrin.

These assays can be performed on untransfected cells, including those that naturally express huntingtin with variable polyglutamine stretches, on cells transfected with a huntingtin encoding sequence, or cells from a transgenic animal expressing a mutant huntingtin sequence (Davies et al., Cell 9:537–548). Because Huntington's Disease affects neurons, in general assays are performed on neurons or neuronally derived cell types (e.g., neuronal cells from a fetus with a mutant huntingtin gene or neuronally-derived cell lines transfected with mutant huntingtin).

Vector and Cell Preparation

In some applications of the invention, stably transfected cells are used that can be induced to express huntingtin protein by the withdrawal or addition of tetracycline, depending on the type of promotor contained in the stable transfectants. Clonal striatal cells, cortical cells, or other hybrid cells derived from fusions of neuronal cells with a proliferating cell (e.g., neuroblastoma (Wainwright et al., J. Neurosci. 15:676–688, 1995) are treated to stably express a plasmid encoding a tetracycline (tet)-inducible promotor such as pUHD10-3 (Gossen and Bujard, Proc. Natl. Acad. Sci. USA 89:5547–5551, 1992; Clontech, Tet-on or Tet-off Gene Expression Systems). Vectors encoding huntingtin cDNAs with variable polyglutamines (e.g., 18, 46, and 100 glutamines) are stably transfected into these cells. Alternatively, double stable transfectants carrying pUHD10-3 and pTK-Hyg (Clontech) containing FLAG-huntingtin cDNAs are established. Huntingtin expression can be induced when the tetracycline derivative Doxycycline (2 μg/ml) is introduced (Tet-on) or omitted (Tet-off) from the medium (e.g., for one day). The optimal time for induction of mutant huntingtin expression is determined by Western blot assay.

Transfection of cells can be carried out by methods known in the art. For example, Lipofectamine (Gibco/BRL) can be used. In such a protocol, cells that are about 70% confluent are transfected according to the manufacturer's instructions using, for example, pcDNA3 as the parent plasmid for a transient transfection, or pUHD10-3 for use with the Tet-on/Tet-off system described herein. In the case of transient transfection, the pCNH2hygro plasmid used for selection in the manufacturer's protocol is omitted as is the addition of hygromycin to the medium.

To prepare a vector encoding mutant huntingtin, cDNAs are constructed that encode partial (e.g., 3 kb) or full-length huntingtin (9.4 kb) transcripts with variable polyglutamine regions (e.g., 18, 46, and 100 glutamines). The cDNAs can contain an N-terminal FLAG sequence upstream of huntingtin to permit native distinction of native and expressed huntingtin. The cDNAs are cloned into the mammalian expression vector pcDNA3 for transient transfection or pUHD10-3 for use with a tet-regulated promotor plasmid in stable transfectants. Transfections with Lipofectamine are performed using, for example, 2.5 µg plasmid DNA. Biochemical and immunofluorescence analysis with anti-FLAG antisera (Kodak) is performed to examine the presence of the FLAG-huntingtin fusion proteins.

The assays used in the invention are performed by, for example, obtaining cells expressing either a mutant or normal (or both) huntingtin protein as described above. The cells are serum-starved for 1 hour and harvested at room temperature into PBS containing 5 mM EDTA. The cells are pelleted and resuspended in PBS containing 1 mM $CaCl_2$, 1 mM $MgCl_2$ 5 mM glucose and 0.2% bovine serum albumin (BSA). These perforated cells are incubated at 37° C. in biotinylated transferrin (2 µg/ml; Sigma Chemical Co.) for up to 15 minutes and then washed and returned to ice and pelleted. The supernatant is aspirated and the pellets used for either internalization or sequestration assays.

Internalization Assay

The internalization of b-transferrin is measured by the acquisition of its resistance to MesNa, which occurs as a result of its inclusion into sealed coated vesicles. The cell pellets are resuspended in 50 µl of 10 mM MesNa gently mixed and incubated for 30 minutes on ice. Next 12.5 µl of 50 mM MesNa is added and at 60 minutes another 16 µl of 50 mM MesNa is added. The MesNa solutions are prepared in a buffer (100 mM NaCl, 1 mM EDTA, 50 mM Tris, 0.2% BSA, pH 8.6) just before each addition. After 90 minutes, the MesNa is oxidized by adding 25 µl of 500 mM iodoacetic acid (Sigma Chemical Co.). After a ten minute agitation, the membranes are solubilized by adding 0.1 ml blocking buffer (1% Triton® X-100, 0.1%SDS, 0.2% BSA, 50 mM NaCl, 1 mM EDTA, 10 mM Tris, pH 7.4) to each tube and vortexing briefly. 0.1 ml of each sample is plated into a well on a prepared ELISA plate that contained 0.1 ml blocking buffer. Total cell-associated b-transferrin is determined using cells incubated at 37° and subjected to the same buffer additions without MesNa.

An ELISA-based assay is used to detect the internalized b-transferrin using standard methods. For example, after incubating the lysates in the microtiter wells overnight, the wells are washed. Streptavidin-HRP (Boehringer-Mannheim Biochemicals) is diluted (e.g., 1/5,000) in blocking buffer and 0.2 ml is added to each well. The plates are incubated for at least 60 minutes at room temperature. After washing, 0.2 ml of substrate solution (10 mg 0-phenylenediamine, 10 µl $H_2O_2$ in 25 ml of 50 mM $Na_2HPO_4$, 27 mM citrate, pH 5) is added to each well and the incubation allowed to proceed until sufficient color develops, typically 2–4 minutes. The reaction is terminated by adding 50 µl per well of 2 M $H_2SO_4$. The $A_{490}$ is read using an ELISA plate reader and corrected for the $A_{655}$.

Sequestration Assay

The sequestration of b-transferrin which occurs either as a result of its inclusion into sealed, coated vesicles or its inclusion into deeply invaginated coated pits was determined by its acquisition of inaccessibility to the large (68 kD) probe, avidin.

To perform this assay, cell pellets are resuspended in 0.1 ml of 50 µg/ml avidin in KSHM (100 mM K acetate, 85 mM sucrose, 20 mM HEPES, 1 mM Mg acetate, pH 7.4) containing 0.2% BSA. The resuspended pellets are agitated at 4° C. for at least 1 hour. Biocytin (Sigma Chemical Co.; 20 mg/ml in $H_2O$) is then added to a final concentration of 50 µg/ml, and the mixture is agitated for another 10 minutes. The cells are lysed by addition 0.1 ml blocking buffer and briefly vortexing. An aliquot (0.1 ml) of each sample is plated into prepared microtiter wells to which 0.1 ml blocking buffer was added. As with the internalization assay, an ELISA-based assay is performed on the cells to identify the bound b-transferrin.

In the ELISA assays, streptavidin-HRP is applied to the plates to detect the exposed b-transferrin signal. Biotin residues on the b-transferrin that remain available to the avidin are quantitated by densitometry. The ELISA plates used for the assays described above are prepared by plating an anti-transferrin antibody (e.g., rabbit anti-human transferrin IgG (Boehringer Mannheim Biochemicals) at a 1/1,000 dilution) into microtiter wells. The plates are incubated for a suitable amount of time (e.g., overnight at 4° C.), washed, then incubated in blocking buffer.

To analyze the results of an assay, typically, data from six separate experiments are subjected to statistical analysis by two way ANOVA and Bonferoni tests to determine which groups are different at p less than or equal to 0.05. Data from the two types of assay are compared to analyze the amounts of sequestered and internalized b-transferrin.

Additional guidance for the execution of these methods can be found in Carter et al. (J. Cell Biol. 120:37–45, 1993), Smythe et al. (J. Cell Biol. 119:1163–1171, 1992), and Smythe et al. (In Methods in Enzymology, James E. Rothman, Ed., 219:223–234, Academic Press, 1992).

In the invention, the assays described above are used to identify a compound that may be useful in the treatment of diseases that are characterized by the expression of mutant huntingtin. To identify such compounds, a candidate compound (test compound) is added to a cell culture (described above), and incubated with the culture for a suitable amount of time. In general, the amount of test compound in the culture medium is from 0.1 µM to 1 µM. The amount of time that the test compound is incubated with the cells can be from less than 1 minute to 8 hours, preferably is from less than one minute to 30 minutes before serum starvation. The cells are then harvested and assayed for endocytosis as described above. A parallel assay is performed with cells from the same or a sister culture that is not incubated with the test compound. If the rate or total amount of endocytosis is increased in the presence of a given test compound compared to in the absence of the test compound, that compound is potentially useful as a therapeutic for Huntington's Disease (or any other disease caused by expression of mutant huntingtin).

Classes of compounds that can be tested include those that activate GTP-binding proteins or protein kinase C, those that alter the pH of the extracellular environment, and those that alter the concentration of extracellular calcium (especially those that reduce it), or reduce the concentration of intracellular calcium (e.g., calcium channel blockers such as Nifedipine). Other compounds that can be tested include compounds that block NMDA receptors (e.g., MK801, APV), reduce oxidative stress (coenzyme Q), reduce lipid peroxidation, or caspase inhibitors (e.g., Z-VAD-FMK, Z-DEVD-FMK) and other proteases.

Because there can be variability in patient response to a given therapeutic, an assay of endocytosis can be used to determine whether a given therapeutic is useful for treating a particular patient who has been diagnosed as having Huntington's Disease. To perform this assay, cells are collected from the patient, and the level of endocytosis of an appropriate marker (such as biotinylated trnsferrin, biotinylated D1 or D2 receptor agonists, biotinylated substance P, or a biotinylated ligand to any G-protein-coupled receptor) in the cells is assessed by comparing endocytosis in the presence and absence of the compound. The cells can be any cell type that expresses huntingtin, for example, a lymphoblast or a fibroblast. Preferably the cells are neuronally derived, for example fetal cells from an HD gene carrier or a neuronal cell line transfected with a mutant HD gene. If endocytosis is increased in the presence of any given compound, that compound is potentially useful for treating the patient. Given the long time course of HD, knowing in advance whether a given therapeutic will be effective in a particular patient would be helpful in devising a course of therapy for the patient.

Other Embodiments

It is to be understood that while the invention has been described in conjuction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that affects clathrin-mediated endocytosis in a test cell containing a mutant huntingtin gene comprising an expanded number of CAG repeats, the method comprising
   (a) contacting the test cell with a test compound, wherein the test compound activates protein kinase C and is a phorbol ester; and
   (b) monitoring vesicle formation, vesicle trafficking, or both, in the test cell in the presence of the test compound, wherein a difference in vesicle formation, vesicle trafficking, or both, relative to that in a test cell that has not been contacted with the test compound, indicates that the compound affects clathrin-mediated endocytosis in the cell.

2. The method of claim 1, wherein the test cell is a neuron.

3. A method of identifying a compound that affects clathrin-mediated endocytosis in a test cell containing a mutant huntingtin gene comprising an expanded number of CAG repeats, the method comprising
   (a) contacting the test cell with a test compound, wherein the test compound alters the concentration of extracellular calcium; and
   (b) monitoring vesicle formation, vesicle trafficking, or both, in the test cell in the presence of the test compound, wherein a difference in vesicle formation, vesicle trafficking, or both, relative to that in a test cell that has not been contacted with the test compound, indicates that the compound affects clathrin-mediated endocytosis in the cell.

4. The method of claim 3, wherein the test compound activates protein kinase C.

5. The method of claim 3, wherein the test cell is a neuron.

6. A method of identifying a compound that affects clathrin-mediated endocytosis in a test cell containing a mutant huntingtin gene comprising an expanded number of CAG repeats, the method comprising
   (a) contacting the test cell with a test compound, wherein the test compound is a phorbol ester; and
   (b) monitoring vesicle formation, vesicle trafficking, or both in the test cell in the presence of the test compound, wherein a difference in vesicle formation, vesicle trafficking, or both relative to that in a test cell that has not been contacted with the test compound and the test compoud decreases the level of clathrin-mediated endocytosis in the test cell indicates that the compound affects clathrin-mediated endocytosis in the cell.

7. A method of identifying a compound that affects clathrin-mediated endocytosis in a test cell containing a mutant huntingtin gene comprising an expanded number of CAG repeats, the method comprising
   (a) contacting the test cell with a test compound, wherein the test compound alters the concentration of extracellular calcium; and
   (b) monitor vesicle formation, vesicle trafficking, or both in the test cell in the presence of the test compound, wherein a difference in vesicle formation, vesicle trafficking, or both relative to that in a test cell that has not been contacted with the test compound and the test compound decreases the level of clathrin-mediated endocytosis in the test cell indicates that the compound affects clathrin-mediated endocytosis in the cell.

* * * * *